(12) United States Patent
Rantala

(10) Patent No.: US 8,836,514 B2
(45) Date of Patent: Sep. 16, 2014

(54) METHOD FOR HANDLING PRESSURE CHANGES IN INVASIVE BLOOD PRESSURE MONITORING, APPARATUS FOR BLOOD PRESSURE MONITORING, AND COMPUTER PROGRAM PRODUCT FOR BLOOD PRESSURE MONITORING APPARATUS

(75) Inventor: Borje Rantala, Helsinki (FI)

(73) Assignee: General Electric Company, Schenectady, NY (US)

( * ) Notice: Subject to any disclaimer, the term of this patent is extended or adjusted under 35 U.S.C. 154(b) by 236 days.

(21) Appl. No.: 13/457,651

(22) Filed: Apr. 27, 2012

(65) Prior Publication Data

US 2013/0285812 A1   Oct. 31, 2013

(51) Int. Cl.
   *G08B 21/00*   (2006.01)
(52) U.S. Cl.
   USPC ............... 340/573.1; 340/691.3; 600/324
(58) Field of Classification Search
   CPC ..... A61B 5/021; A61B 5/205; A61B 5/14551
   USPC .......... 340/539.12, 573.1, 286.07, 691.3; 600/322, 323, 324; 128/905
   See application file for complete search history.

(56) References Cited

U.S. PATENT DOCUMENTS 8,203,438 B2 *   6/2012   Kiani et al. ............... 340/286.07
2011/0270058 A1 *  11/2011   Price et al. .................... 600/324

* cited by examiner

*Primary Examiner* — Jeffery Hofsass
(74) *Attorney, Agent, or Firm* — Andrus Intellectual Property Law, LLP

(57) ABSTRACT

A method for handling sudden and substantial pressure changes in invasive arterial blood pressure monitoring, a blood pressure monitoring apparatus, and a computer program product for a blood pressure monitoring apparatus are disclosed. To provide a user of a patient monitor a possibility to readily adapt the alarm functionality of blood pressure measurement to a clinical task without a need to go through a complicated nullifying process of a high priority alarm, a touchable user interface element is produced onto a touch screen of patient monitor if a sudden and substantial change is detected in measured arterial blood pressure of the subject. The user interface element is indicative of an alarm and configured to enable the user to modify alarm functionality of the patient monitor for an intentional clinical task that caused the sudden and substantial change in the measured arterial blood pressure.

13 Claims, 2 Drawing Sheets

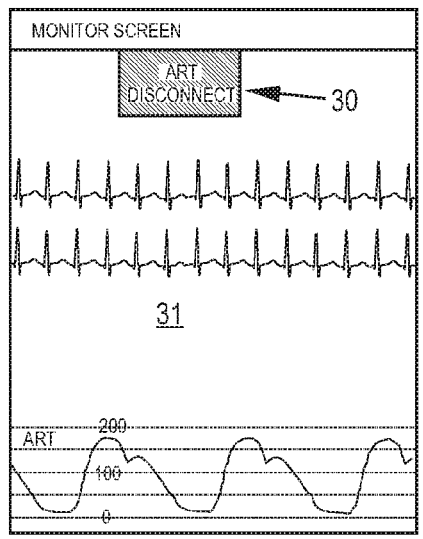
FIG. 3
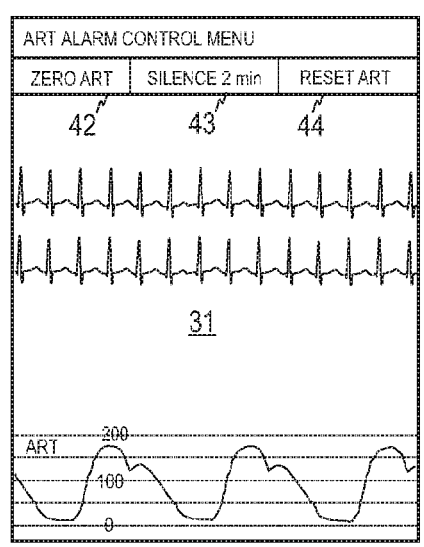
FIG. 4
FIG. 5
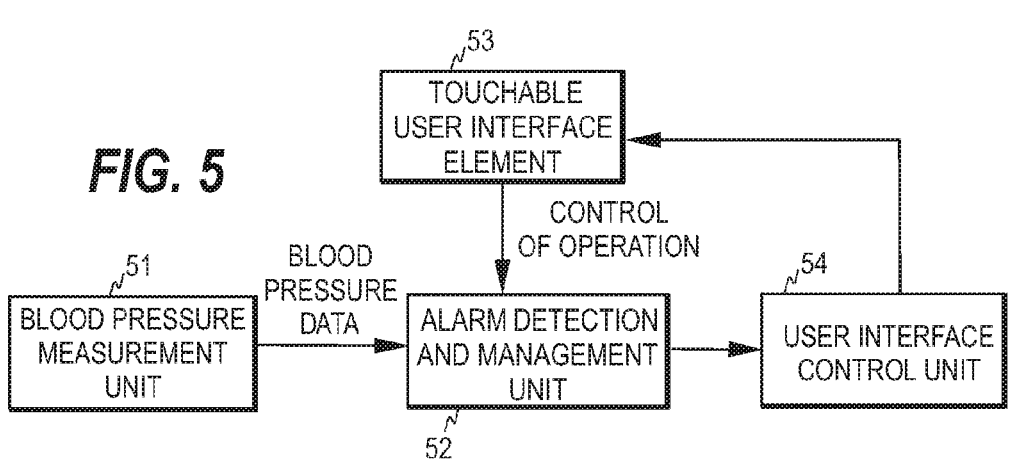

METHOD FOR HANDLING PRESSURE CHANGES IN INVASIVE BLOOD PRESSURE MONITORING, APPARATUS FOR BLOOD PRESSURE MONITORING, AND COMPUTER PROGRAM PRODUCT FOR BLOOD PRESSURE MONITORING APPARATUS

BACKGROUND OF THE INVENTION

This disclosure relates generally to invasive monitoring of arterial blood pressure of a subject. More particularly, this disclosure relates to control of alarm functionality in invasive monitoring of arterial blood pressure.

Although most blood pressure measurements are made non-invasively, invasive blood pressure measurement is used when continuous tracking of blood pressure is required and when accurate information about the waveform of blood pressure is required. Invasive blood measurement is typically used in connection with surgical procedures and in intensive care units (ICUs).

Invasive blood pressure measurement is carried out with an intravascular cannula by placing the needle of the cannula in an artery, typically in a peripheral artery. These intravenous cannulas are typically provided with a three way stopcock that allows, for example, arterial blood samples to be taken from the subject in the middle of the blood pressure monitoring process.

Upcoming international standards on invasive blood pressure measurement mandate a high priority alarm in 10 seconds if arterial pressure falls below 10 mmHg. This is because such a sudden pressure drop may be caused by a disconnected cannula/catheter, which may in turn lead to a blood loss and develop a hazardous situation for the patient within a short time. However, the standards also recognize that certain clinical tasks, such as pressure zeroing and blood sampling, may also result in this alarm, since the tasks may cause the above-mentioned alarm condition to be fulfilled. Nevertheless, high priority alarm is still required in these events since it is regarded that the benefit of a rapid alarm exceeds the disadvantage caused by the false alarms that result from normal clinical procedures.

Although the false alarms may be prevented by inactivation of the alarm functionality or by disabling blood pressure alarm signals, they still are nuisance alarms that require additional measures before and/or after the clinical task that causes the false alarm. That is, if a false alarm is to be avoided, some kind of inactivation of the alarm functionality is needed before the task. Further, restoration of the alarm functionality is normally needed after the task to return to the normal situation. If the false alarm is allowed, additional measures are needed in response to the alarm to return the patient monitor back to normal state.

Thus, normal clinical workflow may include several tasks that drop the measured blood pressure temporarily to zero. Such occasions include zeroing and/or leveling of the pressure transducer and taking blood samples, for example. The requirement of an alarm in response to a sudden blood pressure drop leads in connection with these tasks to situations in which the nursing staff needs to take complicated additional measures either to avoid a false alarm or to acknowledge a false alarm, since the patient monitor has no intrinsic intelligence to sort out alarms that are caused intentionally by the nursing staff. This complicates the work of the nursing staff, especially as the high priority alarm may be persistent and may thus, depending on the alarm logic, reappear after a while.

BRIEF DESCRIPTION OF THE INVENTION

The above-mentioned problem is addressed herein which will be comprehended from the following specification. In order to reduce the complexity involved in nullifying false high priority alarms, the patient monitor is adapted to generate, in response to a detected sudden and substantial pressure change, an alarm notification in the form of a touchable user interface element that allows the user to readily accommodate the alarm functionality of the patient monitor to the normal clinical workflow in case of an intentionally caused change in the measured blood pressure.

In an embodiment, a method for handling sudden pressure changes in invasive arterial blood pressure monitoring comprises invasively measuring arterial blood pressure of a subject through a patient monitor provided with a touch screen and producing a touchable user interface element onto the touch screen if a sudden and substantial change is detected in measured arterial blood pressure of the subject, wherein the user interface element is indicative of an alarm and configured to enable a user of the patient monitor to modify alarm functionality of the patient monitor for an intentional clinical task that caused the sudden and substantial change in the measured arterial blood pressure.

In another embodiment, a physiological monitoring apparatus for monitoring blood pressure of a subject comprises a blood pressure measurement unit adapted to invasively measure arterial blood pressure of a subject and an alarm detection and management unit adapted to produce a touchable user interface element onto a touch screen if a sudden and substantial change is detected in measured arterial blood pressure of the subject, wherein the user interface element is indicative of an alarm and configured to enable a user of the apparatus to modify alarm functionality of the apparatus for an intentional clinical task that caused the sudden and substantial change in the measured arterial blood pressure.

In a still further embodiment, a computer program product on a non-transitory computer-readable medium for a blood pressure monitoring apparatus comprises a program product portion configured to produce a touchable user interface element onto a touch screen if a sudden and substantial change is detected in measured arterial blood pressure of the subject, wherein the user interface element is indicative of an alarm and configured to enable a user of the apparatus to modify alarm functionality of the apparatus for an intentional clinical task that caused the sudden and substantial change in the measured arterial blood pressure.

Various other features, objects, and advantages of the invention will be made apparent to those skilled in the art from the following detailed description and accompanying drawings.

BRIEF DESCRIPTION OF THE DRAWINGS

FIG. 3 illustrates an example of the touchable user interface element generated in response to a sudden drop in measured blood pressure;

FIG. 4 illustrates an example of the user menu displayed in response to the touching of the user interface element of FIG. 3; and FIG. 5 illustrates an example of the functional entities of a patient monitor in terms of handling of sudden pressure changes in invasive arterial blood pressure monitoring.

DETAILED DESCRIPTION OF THE INVENTION

Figure 1:
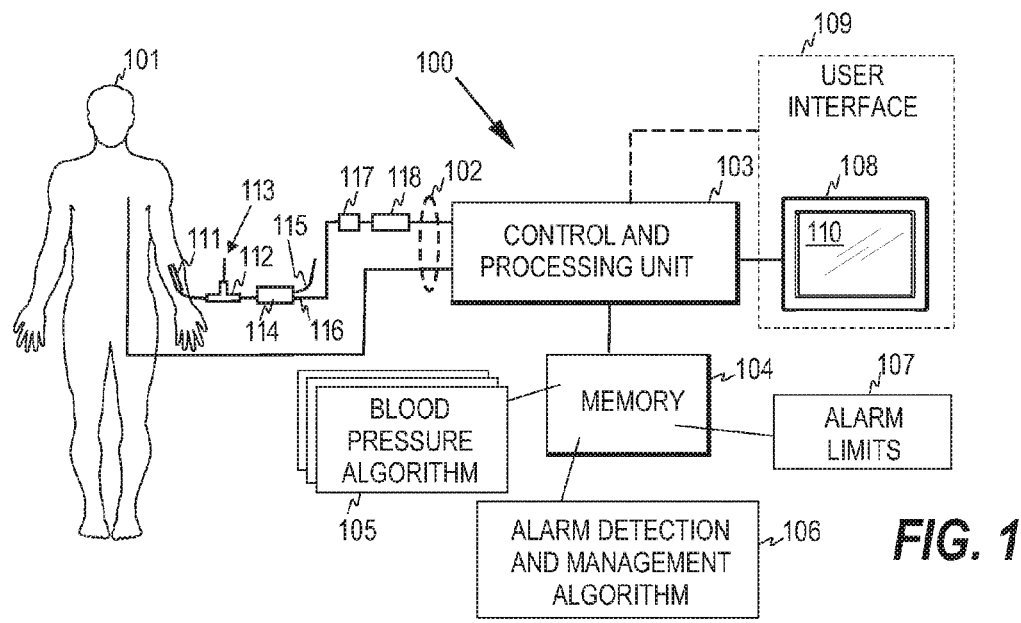
FIG. 1 illustrates one embodiment of an apparatus for monitoring patients.

FIG. 1 illustrates one embodiment of a physiological monitoring apparatus/system 100 for monitoring a subject/patient 101. A monitoring apparatus/system normally acquires a plurality of physiological signals 102 from the subject, where one physiological signal corresponds to one measurement channel. The physiological signals typically comprise several types of signals, such as blood pressure, ECG, EEG, respiration, and plethysmographic signals. Based on the raw real-time physiological signal data obtained from the subject, a plurality of physiological parameters may be determined, each physiological parameter being calculated from the waveform data of one or more of the physiological signals acquired from the subject.

The physiological signals 102 acquired from the subject are supplied to a control and processing unit 103 through a pre-processing stage (not shown) comprising typically an input amplifier and a filter, for example. The control and processing unit converts the signals into digitized format for each measurement channel. The digitized signal data may then be stored in the memory 104 of the control and processing unit. The digitized signal data is utilized by parameter algorithms 105 adapted to record, when executed by the control and processing unit, the time series of the physiological parameters to be monitored. The obtained time series of the physiological parameters may be stored in the memory.

Since the above problem of false alarms relates to (invasive) measurement of blood pressure, the physiological monitoring apparatus/system 100 is discussed below in terms of blood pressure measurement. FIG. 1 illustrates typical components of invasive blood measurement. A catheter/cannula 111 is placed in an artery and connected through flexible tubing to a three-way stopcock 112 used to take blood samples and zero the pressure sensor through port 113. The stopcock is further connected to a flushing valve 114 comprising a port 115 for a fluid bag (not shown) and a port 116 connected to the pressure sensor/transducer 117. A small fluid flow is used to flush the catheter to prevent blood clotting at the catheter tip, with occasional larger boluses if clotting is detected. The pressure sensor is connected to an electric processing unit 118 comprising a preamplifier.

Blood pressure parameter algorithm 105 may thus retrieve the blood pressure waveform data from the electric processing unit 118 and store the obtained blood pressure time series in memory 104. The control and processing unit may further use an alarm detection and management algorithm 106 to detect alarm events, to produce alarm notifications, and to manage the alarms. The algorithm 106 analyzes the blood pressure time series and decides, based on the analysis and other input information, when an alarm is detected. The memory may also store a plurality of alarm limits 107 for making the alarm decisions. Algorithm 106 may further decide whether or not an alarm notification is to be produced in response to a detected alarm. The algorithm may also handle an alarm detected, i.e. escalate and/or terminate the alarm.

In logical sense the alarm functionality implemented by the alarm generation and management algorithm may be regarded to comprise several alarm modes for the blood pressure measurement; a normal alarm mode used to alert the nursing staff to patient blood pressure changes and at least one technical alarm state that may be used when an intentionally or unintentionally caused substantial change in the measured blood pressure generates an alarm. The term "technical alarm" here refers to an alarm resulting from a technical (i.e. non-physiological) issue, such as a clinical task, which causes a sudden and substantial change in measured blood pressure. Such tasks include zeroing and blood sampling, which suddenly drop the measured blood pressure, and manual flushing of the catheter, which causes a sudden and substantial increase in the measured pressure.

In the normal alarm mode, algorithm 106 is adapted to generate an alarm if a sudden and substantial change is detected in the arterial blood pressure. The alarm may be a high priority alarm, the handling/escalation of which may depend on user actions. In addition to the visual and/or audible effects possibly produced at a detected alarm event, an alarm may also be transmitted to an external monitoring unit through a network, for example. In the technical alarm state, normal alarm functionality is terminated or modified, i.e. a transition from the normal mode to a technical alarm state cancels the generated alarm and the processing thereof. Transition from the normal alarm mode to a technical alarm state is made possible through a touchable alarm notification generated onto a touch screen in response to the detection of a sudden drop (or rise, in the case of manual flushing) in the arterial blood pressure.

The control and processing unit 103 is further configured to control the display unit 108 of the apparatus. A display control algorithm may be stored in the memory of the control and processing unit. The user may supply information and control the apparatus/system through user interface 109 that may include various input/output devices. As indicated above, the display unit is provided with a touch screen 110. That is, the touch screen is a user interface component. The above-mentioned control involves that the control and processing unit is adapted to produce a user interface element onto the touch screen in response to a sudden and substantial blood pressure change detected in the normal alarm mode, and that the user may access the alarm functionality by touching the user interface element. In other words, the touching of the user interface element makes various control options, termed technical alarm response options in this context, available to the user. Selection of a technical alarm response option results in modification of normal alarm functionality, i.e. a transition from the normal alarm mode to a technical alarm state occurs in response to the selection.

Although the patient monitor typically measures several types of physiological signals simultaneously, it may also comprise invasive blood pressure measurement only.

Figure 2:
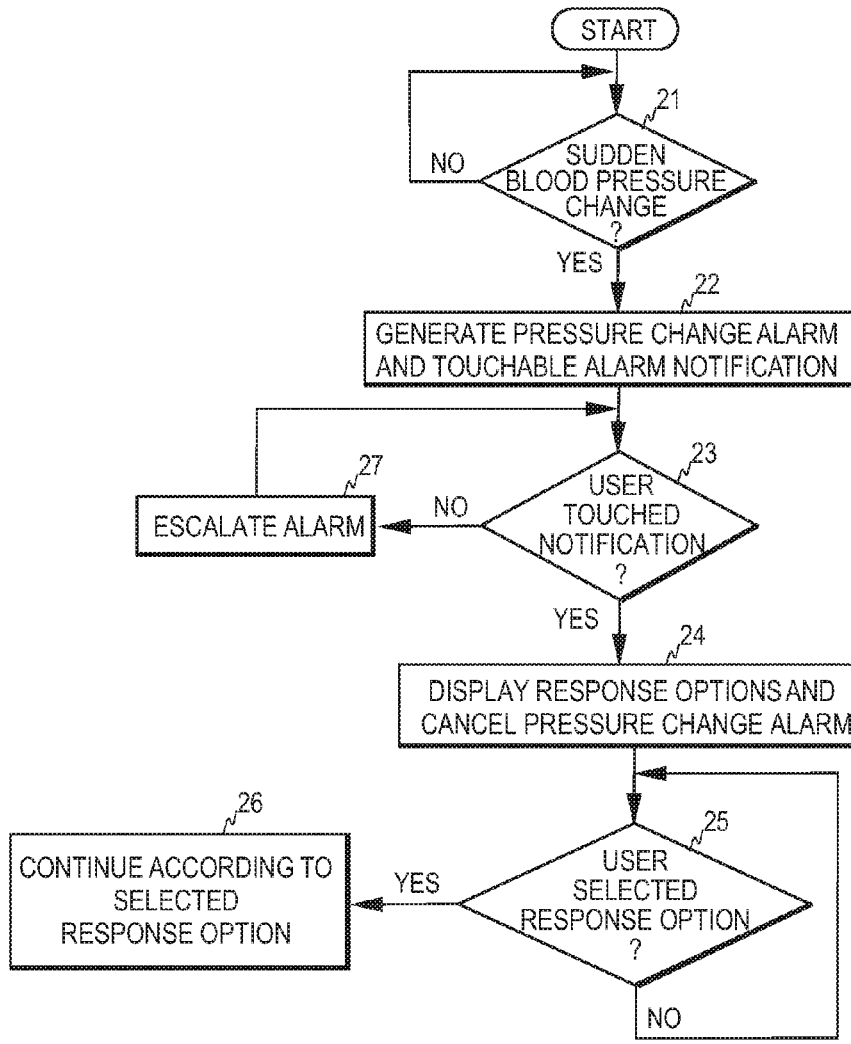
FIG. 2 is a flow diagram illustrating an embodiment of the handling of sudden pressure changes in the apparatus of FIG. 1.

FIG. 2 is a flow diagram illustrating one embodiment of the handling of a detected sudden and substantial pressure change in the arterial blood pressure. If algorithm 106 detects a sudden pressure drop or rise (step 21/yes), it generates an alarm and an alarm notification which is displayed on the touch screen of the display unit (step 22) so that the user can touch the notification. A sudden drop may be detected, for example, if the measured blood pressure drops from normal values (which are typically between 70 and 150 mmHg) below a certain level, such as 10 mmHg, within a short time interval, such as 5 seconds. A further requirement may be that the resulting blood pressure is non-pulsating. A sudden rise may be detected if the measured blood pressure rises above a certain abnormal level, such as 250 mmHg, within in a short time interval, such as 10 seconds. However, the limits of a sudden and substantial change may vary.

The generation of the alarm notification typically includes creation of a user interface element instance that indicates a high priority alarm. FIG. 3 shows an example of a user interface element which is a label or note 30 displayed on the touch screen 31. In the example of the figure, the text of the label indicates a possible disconnection of the arterial catheter/cannula (i.e. the detected change is a sudden drop in the measured blood pressure) and the color of the label may also be indicative of a high priority alarm.

With reference to FIG. 2 again, if the user touches the label 30 (step 23/yes), a menu is opened that includes a plurality of technical alarm response options for controlling the alarm functionality of the blood pressure monitoring. Further, in response to the touching, the alarm produced at step 22 is cancelled (step 24). When the user selects (step 25/yes) one of the technical alarm response options by touching the respective option on the screen, the patient monitor continues to operate according to the technical alarm response option selected (step 26). That is, the patient monitor assumes the technical alarm state that corresponds to the selected response option. The technical alarm states may correspond to existing operation modes of the patient monitor. If the user does not touch label 30, the alarm is escalated according to the normal alarm mode (step 27).

FIG. 4 shows an example of a menu 41 opened in response to the touching of user interface element 30, i.e. the menu opened in step 24 of FIG. 2. In this example, the menu comprises three technical alarm response options 42 to 44. The first option 42 refers to normal zeroing of the pressure transducer. Thus, by touching this option on the screen, the user indicates to the patient monitor that the reason for the alarm was the opening of the stopcock due to the establishment of the zero pressure reference value. The second option 43 refers to an alarm mode in which all alarms (or at least the audio) are silenced for 2 minutes. By selecting this alternative, the user may, for example, complete a blood sampling or continue to improve the posture of the patient without having to deal with the alarm raised by the monitor. The third technical alarm response option 44 refers to resetting of the alarm functionality with respect to arterial blood pressure measurement. In this technical alarm state, all alarms are suspended indefinitely but rearmed if the pressure exceeds a certain level, such as 30 mmHg, for a predetermined period, such as 10 seconds. Thus, technical alarm response option 43 eliminates all alarms for a predetermined time (2 minutes), while technical alarm response option 44 eliminates all alarms until normal state is restored. The user may select the desired option depending on the clinical task concerned.

In terms of the alarm detection and management, the functionalities of the control and processing unit 103 may be divided, in logical sense, into several functional entities shown in FIG. 5. A blood pressure measurement unit 51 is configured to measure blood pressure data from the subject. An alarm detection and management unit 52 is configured to control the alarm functionality of the monitor based on the blood pressure data, alarm limits and user input data received from the user interface. The user input data includes the user control commands from the touchable user interface element 53, which control unit 52 to assume different technical alarm states with respect to blood pressure monitoring. The alarm detection and management unit 52 is further configured to control the user interface, and thus also the touchable user interface element 53, through a user interface control unit 54.

The alarm detection and management unit 52 may further be configured to manage each alarm generated. The management includes escalation and termination of alarms, for example. This applies especially to the normal alarm mode, while in the technical alarm states the alarm functionality is subdued to allow a clinical task to continue without a need to deal with, i.e. invalidate, a high priority alarm through the normal (and complicated) nullifying process.

It is to be noted that FIG. 5 illustrates the division of the functionalities of the control and processing unit in logical sense and in view of the alarm functionality of the blood pressure monitoring. In a real apparatus the functionalities may be distributed in different ways between the elements or units of the apparatus. That is, the apparatus may comprise the above functional units only at logical level.

A conventional patient monitor provided with invasive arterial blood pressure measurement and a touch screen may also be upgraded to include a touchable user interface element configured to enable the user to control the alarm functionality of the monitor in the above-described manner. The software module may be delivered, for example, on a data carrier, such as a CD or a memory card, or through a telecommunications network. Since the software module may utilize the blood pressure data determined by the monitor and also existing alarm modes of the monitor, the software module may comprise only the software portions that enable the generation of the user interface element and the technical alarm response options that enable the transition to the desired technical alarm state in response to the user-selected response option. However, the software module may also include new alarm states/modes for the monitor, i.e. alarm states dedicated to certain clinical tasks.

The above-described solution provides a user a possibility to readily adapt the alarm functionality of the blood pressure measurement to a clinical task without a need to go through a complicated nullifying process of a high priority alarm.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for handling sudden blood pressure changes in invasive arterial blood pressure monitoring, the method comprising:
   invasively measuring arterial blood pressure of a subject through a patient monitor provided with a touch screen; and
   producing a touchable user interface element onto the touch screen only when a sudden and substantial change is detected in measured arterial blood pressure of the subject, wherein the user interface element is indicative of an alarm and configured to enable a user of the patient monitor to modify alarm functionality of the patient monitor for an intentional clinical task that caused the sudden and substantial change in the measured arterial blood pressure.

2. The method according to claim 1, wherein the producing includes producing the touchable user interface element, in which the user interface element is configured to open, in response to touching of the user interface element, a menu with a plurality of touchable response options.

3. The method according to claim 2, wherein the producing includes producing the touchable user interface element, in which the plurality of touchable response options represent a corresponding plurality of technical alarm states in which normal alarm functionality of the patient monitor is subdued.

4. The method according to claim 2, wherein the producing includes producing the touchable user interface element, in which the plurality of touchable response options include at least one option from a group of options including a first option for establishment of zero pressure reference value, a second option for eliminating alarms for a predetermined time, and a third option for eliminating alarms until normal monitoring state is restored.

5. The method according to claim 2, further comprising cancelling the alarm in response to the touching of the user interface element.

6. The method according to claim 1, wherein the producing includes producing the touchable user interface element indicative of the alarm, in which the alarm is a high priority alarm.

7. A physiological monitoring apparatus for monitoring blood pressure of a subject, the apparatus comprising:
   a blood pressure measurement unit adapted to invasively measure arterial blood pressure of a subject; and
   an alarm detection and management unit adapted to produce a touchable user interface element onto a touch screen only when a sudden and substantial change is detected in measured arterial blood pressure of the subject, wherein the user interface element is indicative of an alarm and configured to enable a user of the apparatus to modify alarm functionality of the apparatus for an intentional clinical task that caused the sudden and substantial change in the measured arterial blood pressure.

8. The apparatus according to claim 7, wherein the user interface element is configured to open, in response to touching of the user interface element, a menu with a plurality of touchable response options.

9. The apparatus according to claim 8, wherein the plurality of touchable response options represent a corresponding plurality of technical alarm states in which normal alarm functionality of the apparatus is subdued.

10. The apparatus according to claim 8, wherein the plurality of touchable response options include at least one option from a group of options including a first option for establishment of zero pressure reference value, a second option for eliminating alarms for a predetermined time, and a third option for eliminating alarms until normal monitoring state is restored.

11. The apparatus according to claim 8, wherein the alarm detection and management unit is adapted to cancel the alarm in response to the touching of the user interface element.

12. The apparatus according to claim 7, wherein the alarm is a high priority alarm.

13. A computer program product on a non-transitory computer-readable medium for a blood pressure monitoring apparatus, the computer program product comprising:
   a first program product portion configured to produce a touchable user interface element onto a touch screen only when a sudden and substantial change is detected in measured arterial blood pressure of the subject, wherein the user interface element is indicative of an alarm and configured to enable a user of the apparatus to modify alarm functionality of the apparatus for an intentional clinical task that caused the sudden and substantial change in the measured arterial blood pressure.

* * * * *